United States Patent
Kozlowski et al.

(10) Patent No.: US 8,372,422 B2
(45) Date of Patent: *Feb. 12, 2013

(54) HYDROXYAPATITE-TARGETING POLY(ETHYLENE GLYCOL) AND RELATED POLYMERS

(75) Inventors: Antoni Kozlowski, Huntsville, AL (US); Michael J. Roberts, Charlotte, NC (US)

(73) Assignee: Nektar Therapeutics, San Francisco, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 12/899,521

(22) Filed: Oct. 6, 2010

(65) Prior Publication Data

US 2011/0020422 A1 Jan. 27, 2011

Related U.S. Application Data

(63) Continuation of application No. 10/398,845, filed as application No. PCT/US01/32566 on Oct. 18, 2001, now Pat. No. 7,829,074, which is a continuation-in-part of application No. 09/712,536, filed on Nov. 14, 2000, now Pat. No. 6,436,386.

(51) Int. Cl.
*A61F 2/00* (2006.01)
*A61K 31/74* (2006.01)
*A61K 31/00* (2006.01)
*A61K 47/48* (2006.01)
*A61K 31/79* (2006.01)

(52) U.S. Cl. ............... 424/423; 424/78.18; 424/78.3; 424/78.17; 424/78.24

(58) Field of Classification Search ............ 424/78.17, 424/400, 78.18, 78.3, 423; 514/772.4
See application file for complete search history.

(56) References Cited

U.S. PATENT DOCUMENTS

| | | |
|---|---|---|
| 4,642,229 A | 2/1987 | Cumming et al. |
| 4,760,057 A | 7/1988 | Alexander |
| 4,935,465 A | 6/1990 | Garman |
| 5,412,072 A | 5/1995 | Sakurai et al. |
| 5,413,992 A | 5/1995 | Nicolaou et al. |
| 5,561,119 A | 10/1996 | Jacquesy et al. |
| 5,650,234 A | 7/1997 | Dolence et al. |
| 5,840,900 A | 11/1998 | Greenwald et al. |
| 5,880,131 A | 3/1999 | Greenwald et al. |
| 5,955,100 A | 9/1999 | Bosslet et al. |
| 6,146,658 A | 11/2000 | Bosslet et al. |
| 6,436,386 B1 | 8/2002 | Roberts et al. |
| 7,829,074 B2 | 11/2010 | Roberts et al. |

FOREIGN PATENT DOCUMENTS

| | | |
|---|---|---|
| DE | 4236237 | 4/1994 |
| EP | 0201057 | 11/1986 |
| EP | 0 512 844 A1 * | 11/1992 |
| EP | 0512844 | 11/1992 |
| EP | 0595133 | 5/1994 |
| JP | 62-26256 | 2/1987 |
| JP | 02268190 | 11/1990 |
| WO | WO 92/20371 | 11/1992 |
| WO | WO 94/21235 | 9/1994 |
| WO | WO 96/23794 | 8/1996 |
| WO | WO 96/40285 | 12/1996 |
| WO | WO 98/00438 | 1/1998 |
| WO | WO 98/35704 | 8/1998 |
| WO | WO 99/14259 | 3/1999 |
| WO | WO 99/22770 | 5/1999 |
| WO | WO 99/34833 | 7/1999 |
| WO | WO 99/40214 | 8/1999 |
| WO | WO 00/64516 | 11/2000 |
| WO | WO 01/26692 | 4/2001 |
| WO | WO 01/45796 | 6/2001 |
| WO | WO 01/80898 | 11/2001 |
| WO | WO 02/059179 | 8/2002 |

OTHER PUBLICATIONS

Bentley, et al., "Peg-Linked Artemisinin Antimalarials," Polymer Preprints, The Division of Polymer Chemistry, Inc., vol. 38, No. 1, pp. 584-585, (Apr. 1997).
Fujisaki, et al., "Physicochemical Characterization of Bisphosphonic Carboxyfluoroscein for Osteotropic Drug Delivery," The J. of Pharm. and Pharmacol., vol. 48, No. 8, pp. 798-800, (Aug. 1996).
Greenwald, et al., "Highly Water Soluble Taxol Derivatives: 7-Polyethylene Glycol Carbamates and Carbonates," J. Org. Chem., vol. 60, pp. 331-336, (1995).
Greenwald, et al., "Drug Delivery Systems: anticancer prodrugs and their polymeric conjugates," Exp. Opin. on Ther. Patents, vol. 7, No. 6, pp. 601-609, (1997).
Greenwald, et al., "Drug Delivery Systems Employing 1,4- or 1,6-Elimination: Poly(ethylene glycol) Prodrugs of Amine-Containing Compounds," J. Med. Chem., vol. 42, No. 7, pp. 3657-3667, (1999).
Kasugai, et al., "Selective Drug Delivery System to Bone: Small Peptide (Asp)6 Conjugation," J. of Bone and Mineral Research, vol. 15, No. 5, pp. 936-943, (2000).
Lapienis, et al., "Preparation of Monomethyl Ethers of Poly(ethylene glycol)s Free of the Poly(Ethylene Glycol)", in J. of Bioact. and Comp. Poly., vol. 16, No. 3, pp. 206-220, (2001).
Ouchi, et al., "Design of Antitumor Agent-Terminated Poly(Ethylene Glycol) Conjugate as Macromolecular Prodrug," Polymer Preprints, The Division of Polymer Chemistry, Inc., vol. 38, No. 1, pp. 582-583, (Apr. 1997).

(Continued)

*Primary Examiner* — Blessing Fubara
(74) *Attorney, Agent, or Firm* — Mark A. Wilson

(57) ABSTRACT

Isolatable, hydroxyapatite-targeting polymeric structures, and biologically active conjugates thereof, are provided. The polymeric structure includes a linear or branched water-soluble and non-peptidic polymer backbone, such as a PEG backbone, having at least two termini, a first terminus being covalently bonded to a hydroxyapatite-targeting moiety, such as a bisphosphonate, and a second terminus covalently bonded to a chemically reactive group, wherein said chemically reactive group is protected or unprotected. Methods of preparing and using hydroxyapatite-targeting polymeric structures, and biologically active conjugates thereof, are also provided.

17 Claims, No Drawings

OTHER PUBLICATIONS

Suzawa, et al., "Synthesis of a Novel Duocarmycin Derivatives DU-257 and its Application to Immunoconjugate Using Poly(ethylene glycol)-dipeptidyl Linder Capable of Tumor Specific Activation," Bioorganic & Med. Chem., vol. 8, pp. 2175-2184, (2000).

Zalipsky, et al., "Attachment of Drugs to Polyethylene Glycols," Eur. Polym. J., vol. 19, No. 12, pp. 1177-1183, (1983).

PCT International Search Report corresponding to PCT Application No. PCT/US2001/032566 date of mailing Oct. 2, 2002.

PCT Written Opinion corresponding to PCT Application No. PCT/US2001/032566 date of mailing Oct. 10, 2002.

PCT International Preliminary Examination Report corresponding to PCT/US2001/032566 date of mailing Feb. 19, 2003.

Bentz, et al., "Improved local delivery of TGF-β2 by binding to injectable fibrillar collagen via difunctional polyethylene glycol", J. Biomed. Mat. Res., vol. 39, pp. 539-548, (1998).

DDS no Shinpo 1995-96 (Advancement in DDS 1995-96), pp. 82-94, published by Nakayama Shoten Co., Ltd., (1995).

Omelyanenko, et al., "Biorecognition of HPMA Copolymer-Adriamycin Conjugates by Lymphocytes Mediated by Synthetic Receptor Binding Epitopes", Pharm. Res., vol. 16, No. 7, pp. 1010-1019, (1999).

Roberts, et al., "Attachment of Degradable Poly(ethylene glycol) to Proteins Has the Potential to Increase Therapeutic Efficacy", J. of Pharm. Sci., vol. 87, No. 11, pp. 1440-1445, (Nov. 1998).

Zhao, et al., Novel Degradable Poly(ethylene glycol) Hydrogels for Controlled Release of Protein, J. of Pharm. Sci., vol. 87, No. 11, pp. 1450-1458, (Nov. 1998).

Zhao, et al., "Novel Degradable Poly(ethylene glycol) Esters for Drug Delivery", in Poly(ethylene glycol) chemistry and biological applications, ACS Symposium series 680, pp. 458-472, (1997).

European Communication corresponding to European Patent Application No. 01 984 000.8 dated Oct. 20, 2005.

European Summons to attend oral proceedings corresponding to European Patent Application No. 01 984 000.8 dated Oct. 16, 2006.

European Summons to attend oral proceedings corresponding to European Patent Application No. 01 984 000.8 dated Feb. 7, 2008.

Japanese Notice of Reasons for Rejection corresponding to Japanese Patent Application No. 2002-542430 mailing date May 28, 2008.

Japanese Notice of Final Rejection corresponding to Japanese Patent Application No. 2002-542430 mailing date Jan. 30, 2009.

Enzon Pharmaceuticals, Macromolecular Engineering Technologies, pp. 1-14, (2004).

Nektar™—Transforming Therapeutics, Nektar Molecule Engineering: Polyethylene Glycol and Derivatives for Advanced PEGylation, pp, 1-20, Catalog—2003, (Jul. 2003).

Nektar™—Transforming Therapeutics, Nektar Advanced PEGylation: Polyethylene Glycol and Derivatives for Advanced PEGylation, pp. 1-24, Catalog—2004, (Jul. 2004).

Nektar™—Transforming Therapeutics, Nektar Advanced PEGylation: Polyethylene Glycol and Derivatives for Advanced PEGylation, pp. 1-30, (Catalog 2005-2006).

NOF Corporation, "PEG Derivatives, Phospholipid and Drug Delivery Materials for Pharmaceuticals", pp. 1-46, Catalogue 2003-1st, (Jan. 2003).

NOF Corporation, "PEG Derivatives, Phospholipid and Drug Delivery Materials for Pharmaceuticals", pp. 1-50, Catalogue 2003-2nd, (Mar. 2004).

NOF Corporation, "PEG Derivatives, Phospholipids and Drug Delivery Materials for Pharmaceutical Products and Formulations", pp. 1-59, Catalogue Ver. 8, (Apr. 2006).

Polypure, Products; PEG amines; PEG acids and amino acids; PEG thiols and disulfides; Biotins, (Apr. 2004).

Polypure, Products; PEG amines; PEG acids and amino acids; PEG thiols and disulfides; Biotins, (Apr. 2005).

Quanta Biodesign, Labeling, Derivatization and Crosslinking Reagents for Biological and Related Materials with dPEG™, pp. 1-38, (Mar. 12, 2004).

Quanta Biodesign, Labeling, Modification and Crosslinking Reagents incorporating our unique monodispersed dPEG™ Technology, pp. 1-31, (Nov. 5, 2004).

Quanta Biodesign, Ltd., Leading innovator, producer and provider of monodisperse discrete PEG™ (dPEG™) derivatives, (Product Catalog), pp. 1-51, (Updated: Jul. 18, 2005).

Quanta Biodesign, Ltd., Leading innovator, producer and provider of monodisperse discrete PEG™ (dPEG™) derivatives, (Product Catalog), pp. 1-51, (Updated: Nov. 17, 2005).

Shearwater Polymers, Inc., Polyethylene Glycol and Derivatives, pp. 1-49, (Catalog—Mar. 1995).

Shearwater Polymers, Inc., Poylethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—Jan. 2000).

Shearwater Corporation, Polyethylene Glycol and Derivatives for Biomedical Applications, pp. 1-17, (Catalog—Jul. 2001).

Inquiry mailed May 10, 2011, corresponding to Japanese Patent Application No. 2002-542430.

Harris, "Synthesis of Heterofunctional PEG", Poly(ethylene glycol) Chemistry, Biotechnical and Biomedical Applications, Chapter 22.4, pp. 377-380 (1992).

* cited by examiner

HYDROXYAPATITE-TARGETING POLY(ETHYLENE GLYCOL) AND RELATED POLYMERS

CROSS REFERENCE TO RELATED APPLICATIONS

This is a continuation of U.S. patent application Ser. No. 10/398,845, filed Aug. 6, 2003, now U.S. Pat. No. 7,829,074, which is a 35 U.S.C. §371 application of International Application No. PCT/US01/32566, filed Oct. 18, 2001, designating the United States, which application is a continuation in part of U.S. patent application Ser. No. 09/712,536, filed Nov. 14, 2000, now U.S. Pat. No. 6,436,386, the disclosures of which are incorporated herein by reference in their entireties.

FIELD OF THE INVENTION

The invention relates to derivatives of poly(ethylene glycol) and related hydrophilic polymers, to methods for their synthesis, and to surfaces and molecules modified by these polymers.

BACKGROUND OF THE INVENTION

Covalent attachment of the hydrophilic polymer poly(ethylene glycol), abbreviated PEG, also known as poly(ethylene oxide), abbreviated PEO, to molecules and surfaces is of considerable utility in biotechnology and medicine. In its most common form, PEG is a linear polymer terminated at each end with hydroxyl groups:

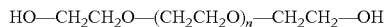

The above polymer, alpha-, omega-dihydroxylpoly(ethylene glycol), can be represented in brief form as HO-PEG-OH where it is understood that the -PEG- symbol represents the following structural unit:

where n typically ranges from about 3 to about 4000.

PEG is commonly used as methoxy-PEG-OH, or mPEG in brief, in which one terminus is the relatively inert methoxy group, while the other terminus is a hydroxyl group that is subject to ready chemical modification. The structure of mPEG is given below.

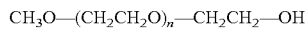

The copolymers of ethylene oxide and propylene oxide are closely related to PEG in their chemistry, and they can be substituted for PEG in many of its applications.

where R=H or alkyl, such as $CH_3$.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., *J. Org. Chem.*, 60:331-336 (1995).

To couple PEG to a molecule, such as a protein, it is often necessary to "activate" the PEG to prepare a derivative of the PEG having a functional group at the terminus. The functional group can react with certain moieties on the protein, such as an amino group, thus forming a PEG-protein conjugate. Many activated derivatives of PEG have been described. An example of such an activated derivative is the succinimidyl succinate "active ester":

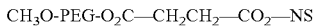

Wherein NS=

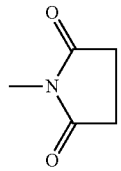

Hereinafter, the succinimidyl active ester moiety will be represented as .

As applications of PEG chemistry have become more sophisticated, there has been an increasing need for heterofunctional PEGs, that is, PEGs bearing dissimilar terminal groups:

X-PEG-Y where X and Y are different groups. Such heterobifunctional PEGs bearing appropriate functional groups may be used to link the PEG to surfaces or biologically active molecules, with the other terminus attached, for example, to a biologically active molecule, a liposome, or a biosensor.

It is desirable in the biotechnical arts to continually develop activated polymers suitable for conjugation with one or more of various substances, including other polymers, peptides, proteins, carbohydrates, oligonucleotides, lipids, liposomes, cells, drugs, surfaces, and other biologically active moieties. Additionally, it would be advantageous to develop activated polymers that can be used for targeting or extended release formulations.

SUMMARY OF THE INVENTION

The invention utilizes hydroxyapatite surfaces, such as bone, for the delivery of biologically active agents with sustained lifetime within the body. Polyethylene glycol is often covalently attached to biologically active molecules to extend its circulation half-life, but the residence time of some conjugates remains suboptimal. There are many biologically active agents, both polypeptides and small drug molecules, that would benefit from the extended residence time within the body and targeting of hydroxyapatite surfaces, such as bone, provided by the invention described more filly below.

The invention provides an isolatable, activated hydroxyapatite-targeting polymeric structure comprising a linear or branched water-soluble and non-peptidic polymer backbone having at least two termini, a first terminus being covalently bonded to a hydroxyapatite-targeting moiety and a second terminus covalently bonded to a chemically reactive group or a protected chemically reactive group. For example, the hydroxyapatite-targeting moiety can be selected from the group consisting of tetracycline, calcein, bisphosphonates, polyaspartic acid, polyglutamic acid, and aminophosphosugars. The chemically reactive group or protected chemically reactive group is preferably selected from the group consisting of hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate. The polymer backbone may comprise, for example, poly(alkylene glycol), poly(oxyethylated polyol), poly(olefinic alcohol), poly(vinylpyrolidone), poly(hydroxypropylmethacrylamide), poly (α-hydroxy acid), poly(vinyl alcohol), polyphosphazene, polyoxazoline, and copolymers, terpolymers, derivatives and mixtures thereof.

By reacting the chemically reactive group with a biologically active agent, the hydroxyapatite-targeting polymers of the invention can be used to tether a biologically active agent to a surface, such as a bone surface. Methods for preparation of the hydroxyapatite-targeting polymers, and biologically active conjugates thereof, are also provided.

In one embodiment, the invention provides a method of utilizing a bone surface in a bone-containing organism, such as a mammal, as a reservoir for a releasable biologically active agent. The method includes providing a hydroxyapatite-targeting, biologically active polymeric structure comprising a linear or branched water-soluble and non-peptidic polymer backbone having at least two termini, a first terminus being covalently bonded to a hydroxyapatite-targeting moiety and a second terminus covalently bonded to a biologically active agent through a linker, wherein at least one of the polymer backbone and the linker comprise a hydrolytically or enzymatically degradable linkage. A therapeutically effective amount of the polymeric structure is administered to a bone-containing organism such that at least a portion of the polymeric structure is bonded to a bone surface by the hydroxyapatite-targeting moiety. Preferably, the hydrolytically or enzymatically degradable linkage is selected from the group consisting of carbonate, carboxylate ester, phosphoester, orthoester, acetal, carbamate, disulfide, and peptide. The hydroxyapatite-targeting polymeric structure with the releasable biologically active agent will initially target bone or bone marrow surfaces within the organism, thereby using the bone surface as a reservoir or depot. The biologically active agent will be released into the organism over time as the degradable linkage degrades.

Thus, the invention allows a biologically active agent to be anchored to a hydroxyapatite surface in vivo and delivered over time to other parts of the organism for treatment of disease. In this manner, the residence time of the biologically active agent could be extended and the efficacy of the treatment improved. In addition, the activated polymer derivatives of the invention are isolatable such that the polymers can be separated and purified prior to attachment to a biologically active agent, thereby increasing yield and purity of the biologically active polymers.

DETAILED DESCRIPTION OF THE INVENTION

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate that the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, preferably indefinitely. Hydrolytically unstable or degradable linkages means that the linkages are degradable in water or in aqueous solutions, including for example, blood. Enzymatically unstable or degradable linkages means that the linkage can be degraded by one or more enzymes.

As used herein, the term "compound" is intended to refer to a chemical entity, whether in the solid, liquid or gaseous phase, and whether in a crude mixture or purified and isolated. The terms "alkyl," "alkene," and "alkoxy" include straight chain and branched alkyl, alkene, and alkoxy, respectively. The term "lower alkyl" refers to $C_1$-$C_6$ alkyl. The term "alkoxy" refers to oxygen substituted alkyl, for example, of the formulas —OR or —ROR$^1$, wherein R and R$^1$ are each independently selected alkyl. The teams "substituted alkyl" and "substituted alkene" refer to alkyl and alkene, respectively, substituted with one or more non-interfering substituents, such as but not limited to, $C_3$-$C_6$ cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like. The term "halogen" includes fluorine, chlorine, iodine and bromine.

"Aryl" means one or more aromatic rings, each of 5 or 6 carbon atoms. Multiple aryl rings may be fused, as in naphthyl or unfused, as in biphenyl. Aryl rings may also be fused or unfused with one or more cyclic hydrocarbon, heteroaryl, or heterocyclic rings. "Substituted aryl" is aryl having one or more non-interfering groups as substituents.

"Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_7$-$C_{12}$ aralkyl, $C_7$-$C_{12}$ alkaryl, $C_3$-$C_{10}$ cycloalkyl, $C_3$-$C_{10}$ cycloalkenyl, phenyl, substituted phenyl, toluoyl, xylenyl, biphenyl, $C_2$-$C_{12}$ alkoxyalkyl, $C_7$-$C_{12}$ alkoxyaryl, $C_7$-$C_{12}$ aryloxyalkyl, $C_6$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{13}$ alkyl), $C_2$-$C_{10}$ thioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-$CF_3$, —C(O)—$CF_3$, —C(O)$NR_2$, —($C_1$-$C_{10}$ alkyl)-S—($C_6$-$C_{12}$ aryl), —C(O)—($C_6$-$C_{12}$ aryl), —$(CH_2)_m$—O—$(CH_2)_m$—O—($C_1$-$C_{10}$alkyl) wherein each m is from 1 to 8, —C(O)$NR_2$, —C(S)$NR_2$, —$SO_2NR_2$, —NRC(O)$NR_2$, —NRC(S)$NR_2$, salts thereof, and the like. Each R as used herein is H, alkyl or substituted alkyl, aryl or substituted aryl, aralkyl, or alkaryl.

The term "amino acid" includes all essential and non-essential amino acids. Standard amino acid abbreviations known in the art are used herein.

The term "biologically active molecule", "biologically active moiety" or "biologically active agent" when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The term "isolatable" is intended to mean that the activated polymers can be isolated or separated from other compounds prior to attachment to a biologically active agent. The acceptable level of isolation or purity will depend on various factors, such as the difficulty of purification, the type of contaminating compounds present, etc. By isolating or separating the hydroxyapatite-targeting activated polymers prior to attachment to the biologically active agent, better yield and purity is achieved. In addition, isolation of the polymer derivatives allows qualitative and quantitative analysis of the polymer prior to incorporation of the biologically active agent, which, in turn, increases the overall quality of the biologically active product. Having an isolatable hydroxyapatite-targeting activated polymer available for attachment to biologically active agents can result in a conjugate with a well-defined composition that can easily be conveyed to regulatory authorities. As exemplified in the examples below, the activated polymer derivatives are generally isolated and purified by precipitation followed by solvent extraction and/or chromatography techniques, such as ion-exchange chromatography.

The invention provides an isolatable hydroxyapatite-targeting polymeric structure comprising a linear or branched water-soluble and non-peptidic polymer backbone having at least two termini, a first terminus being covalently bonded to a hydroxyapatite-targeting moiety and a second terminus covalently bonded to a chemically reactive group, wherein the chemically reactive group is protected or unprotected.

The polymer backbone is a substantially non-immunogenic polymer, such as poly(ethylene glycol) (PEG). However, it should be understood that other related polymers are also suitable for use in the practice of this invention and that the use of the term PEG or poly(ethylene glycol) is intended to be inclusive and not exclusive in this respect. Preferably, the polymer backbone has from 2 to about 300 termini.

PEG is typically clear, colorless, odorless, soluble in water, stable to heat, inert to many chemical agents, does not hydrolyze or deteriorate, and is generally nontoxic. Poly(ethylene glycol) is considered to be biocompatible, which is to say that PEG is capable of coexistence with living tissues or organisms without causing harm. More specifically, PEG is non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —CH$_2$CH$_2$O—(CH$_2$CH$_2$O)$_n$—CH$_2$CH$_2$—, where n is from about 3 to about 4000, preferably from about 3 to about 2000, is one useful polymer in the practice of the invention. Preferably, PEG having a molecular weight of from about 200 Da to about 100,000 Da is used as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched polyethylene glycols can be represented in general form as R(-PEG-OH)$_m$ in which R represents the core moiety, such as glycerol or pentaerythritol, and m represents the number of arms.

Many other polymers are also suitable for the invention. These polymers can be either in linear form or branched form, and include, but are not limited to, other poly(alkylene glycol), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, and copolymers, terpolymers, derivatives and mixtures thereof. Although the molecular weight of each chain of the polymer backbone can vary, it is typically in the range of from about 100 Da to about 100,000 Da, preferably from about 6,000 Da to about 80,000 Da.

Those of ordinary skill in the art will recognize that the foregoing list for substantially water soluble non-immunogenic polymer backbone is by no means exhaustive and is merely illustrative, and that all polymeric materials having the qualities described above are contemplated.

The hydroxyapatite-targeting moiety may comprise any moiety capable of binding to, or otherwise exhibiting a chemical affinity for, hydroxyapatite surfaces (i.e., calcium phosphate), such as bone. The hydroxyapatite-targeting moiety is preferably capable of binding to any hydroxyapatite or calcium phosphate surface. In one embodiment, the hydroxyapatite-targeting moiety is selected from the group consisting of tetracycline, calcein, bisphosphonates, polyaspartic acid, polyglutamic acid, and aminophosphosugars. In a particularly preferred embodiment, the hydroxyapatite-targeting moiety is a bisphosphonate.

An example of a bisphosphonate suitable for use with the invention is shown below.

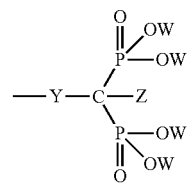

wherein Y and Z are independently selected from the group consisting of hydrogen, —OH, halogen, aryl, substituted aryl, pyridyl, furanyl, pyrrolidinyl, imidazonyl, C1-C30 alkyl, C1-C30 substituted alkyl, NH$_2$, NHR', NR'$_2$, SH, and SR', where R' is C1-C30 alkyl, C1-C10 alkoxy, aryl or substituted aryl, and W is selected from the group consisting of hydrogen, alkyl, substituted alkyl, aryl, substituted aryl, Na$^+$, and K$^+$. Preferably, Y is —NH(CH$_2$)$_p$—, where p is about 2 to about 6, Z is —OH, and each W is hydrogen. A particularly preferred bisphosphonate is 3-amino-1-hydroxypropane-1,1-diphosphonic acid.

Bisphosphonates are characterized by two carbon-phosphorous bonds, the carbon atom replacing the oxygen in the P—O—P (phosphorous-oxygen-phosphorous) bond of pyrophosphate and the P—C—P bond conferring resistance to chemical and enzymatic hydrolysis. Different substitutions on the carbon atom have created several different bisphosphonates, each with its own pharmacological properties. Etidronate, which contains a hydroxyl and methyl group substitution on the carbon atom, was the first bisphosphonate with a half-life in bone of greater than 90 days to be used therapeutically. Other more potent bisphosphonates have subsequently been developed, such as alendronate, which has an alkyl amine and hydroxyl group substitution on the carbon atom.

Bisphosphonates have a strong affinity for hydroxyapatite crystals and, in fairly high doses, inhibit calcification of bone in vivo by physicochemical mechanisms. Bisphosphonates are not metabolized, and seem to be absorbed, excreted, and stored unchanged. However, the side chains of some analogs of bisphosphonates may be modified. Plasma clearance is rapid (half-life around 2 hours) because of the rapid uptake of 20-60% of the absorbed fraction into the skeleton. The remainder is excreted in the urine. The half-life in bone is very long, with release of bisphosphonates occurring only after resorption of bone into which the compounds have been taken up.

The strong affinity of bisphosphonates, and other hydroxyapatite-targeting moieties, for bone enables the polymers of the invention to be used as hydroxyapatite-targeting delivery systems for biologically active agents. Preferably, the isolatable, activated hydroxyapatite-targeting polymers can be efficiently attached to the biologically active agent in a single step.

As noted above, the hydroxyapatite-targeting polymeric structure of the invention has at least one terminus bonded to a protected or unprotected chemically reactive group. The chemically reactive group is preferably suitable for attachment to a functional group on a biologically active agent. Examples of suitable chemically reactive groups include hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate.

As would be understood in the art, the term "protected" refers to the presence of a protecting group or moiety that prevents reaction of the chemically reactive group under certain reaction conditions. The protecting group will vary depending on the type of chemically reactive group being protected. For example, if the chemically reactive group is an amine or a hydrazide, the protecting group is preferably selected from the group of tert-butyloxycarbonyl (t-Boc) and 9-fluorenylmethoxycarbonyl (Fmoc). If the chemically reactive group is a thiol, the protecting group is preferably orthopyridyldisulfide. If the chemically reactive group is a carboxylic acid, such as butanoic or propionic acid, or a hydroxyl group, the protecting group is preferably benzyl. Other protecting groups known in the art may also be used in the invention.

In one embodiment, the chemically reactive groups are selected from the group consisting of hydroxyl, protected hydroxyl, amine, protected amine, carboxylic acid, protected carboxylic acid, maleimide, active carbonates, such as N-hydroxysuccinimidyl carbonates and 1-benzotriazolyl carbonates, and active esters, such as N-hydroxysuccinimidyl esters and 1-benzotriazolyl esters.

One useful hydroxyapatite-targeting polymer has the following general structure:

Q-POLY-L-T wherein POLY is a water-soluble and non-peptidic polymer, Q is a protected or unprotected chemically reactive group, L is a linker, and T is a hydroxyapatite-targeting moiety. Preferably, POLY is a poly(alkylene glycol), such as poly(ethylene glycol), having an average molecular weight from about 200 Da to about 100,000 Da, and T is a bisphosphonate. The linker L is the residue of the functional group used to attach the hydroxyapatite-targeting moiety to the polymer backbone. For example, the linker L may be a hydrolytically stable linkage selected from the group consisting of ether linkages, thio-ether linkages, amide linkages, amine linkages, urea linkages, or carbamate linkages. The linker L may also be a degradable linkage as described in more detail below.

In another embodiment, the hydroxyapatite-targeting polymer has the following general structure:

Q-PEG-L-T wherein PEG is a poly(ethylene glycol) having an average molecular weight from about 200 Da to about 100,000 Da, Q is a protected or unprotected chemically reactive group, L is a linker, and T is a bisphosphonate. Advantageously, PEG is —$CH_2CH_2O$—$(CH_2CH_2O)_n$—$CH_2CH_2$—, wherein n is about 3 to about 2000.

In a third embodiment, the hydroxyapatite-targeting polymer has the following general structure:

T-L-$POLY_a$-R(-$POLY_b$-X)$_q$ wherein
$POLY_a$ and $POLY_b$ are water-soluble and non-peptidic polymer backbones that may be the same or different;

each X is independently selected from the group consisting of alkoxy, substituted alkoxy, aryloxy, substituted aryloxy, hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, and -L-T, with the proviso that at least one X is not -L-T;

R is a central core molecule, such as an amino acid or a polyol;

L is a linker;

T is a hydroxyapatite-targeting moiety; and q is an integer from 2 to about 300.

Preferably, $POLY_a$ and $POLY_b$ are both poly(ethylene glycol) and R is selected from the group consisting of trimethylolpropane, di-rimethylolpropane, glycerol, pentaerythritol, sorbitol, lysine, and di-lysine.

Some examples of preferred embodiments of the hydroxyapatite-targeting polymers of the invention are provided as follows:

PEG(2,000)-α-amine-ω-AHPDP,
PEG(2,000)-α-N-maleimido-ω-AHPDP,
PEG(2,000)-α-AHPDP-ω-propionic acid,
PEG(2,000)-α-AHPDP-ω-propionic acid, N-hydroxysuccinimide ester,
PEG(2,000)-α-AHPDP-ω-protein,
PEG(2,000)-α-$_L$-tyrosine-ω-AHPDP, and
PEG(10,000)-(α-AHPDP)$_4$ where -AHPDP represents 3-amino-1-hydroxypropane-1,1-diphosphonic acid.

The invention also includes conjugates of the hydroxyapatite-targeting polymers of the invention and biologically active agents. For example, the invention provides hydroxyapatite-targeting, biologically active polymers of the following general structure:

D-L'-POLY-L-T wherein POLY is a water-soluble and non-peptidic polymer, D is a biologically active agent, L and L' are linkers which may be the same or different, and T is a hydroxyapatite-targeting moiety.

In another embodiment, the invention provides hydroxyapatite-targeting, biologically active polymers of the following general structure:

D-L'-PEG-L-T wherein PEG is a poly(ethylene glycol) having an average molecular weight from about 200 Da to about 100,000 Da, D is a biologically active agent, L and L' are linkers which may be the same or different, and T is a bisphosphonate.

Further, the invention includes hydroxyapatite-targeting, biologically active polymers of the following general structure:

T-L-POLY$_a$-R(-POLY$_b$-L'-A)$_q$ wherein

POLY$_a$ and POLY$_b$ are water-soluble and non-peptidic polymer backbones that may be the same or different;

each A is independently selected from the group consisting of hydroxyapatite-targeting moieties and biologically active agents, with the proviso that at least one A is a biologically active agent;

R is a central core molecule such as an amino acid or polyol;

L and L' are linkers which may be the same or different;

T is a hydroxyapatite-targeting moiety; and q is an integer from 2 to about 300.

A method of utilizing a hydroxyapatite surface, such as bone, as a reservoir for a releasable biologically active agent is also provided by the invention. The method includes providing a hydroxyapatite-targeting, biologically active polymeric structure comprising a linear or branched water-soluble and non-peptidic polymer backbone having at least two termini, a first terminus being covalently bonded to a hydroxyapatite-targeting moiety and a second terminus covalently bonded to a biologically active agent through a linker, wherein at least one of the polymer backbone and the linker comprises a hydrolytically or enzymatically degradable linkage. For example, in any of the structures given above for the biologically active polymers, the L, L', POLY or PEG moieties may include a hydrolytically or enzymatically degradable linkage therein. For example, PEG can be prepared with ester linkages in the polymer backbone that are subject to hydrolysis. This hydrolysis results in cleavage of the polymer into fragments of lower molecular weight, as shown below.

-PEG-CO$_2$-PEG+H$_2$O→-PEG-CO$_2$H+HO-PEG

Preferably, the hydrolytically or enzymatically degradable linkage is selected from the group consisting of imine, carbonate, carboxylate ester, phosphoester, orthoester, acetal, carbamate linkages of the formula

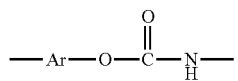

where Ar is an aryl group, disulfide, and peptide. However, other degradable linkages known in the art may be used.

A therapeutically effective amount of the polymeric structure is administered to, for example, a bone-containing mammal, such that at least a portion of the polymeric structure is bonded to a bone surface by the hydroxyapatite-targeting moiety. The hydroxyapatite-targeting polymeric structure, with the releasable biologically active agent attached thereto, will initially target bone surfaces within the organism, thereby using the bone surface as a reservoir or depot. Due to the presence of the degradable linkage in either the polymer backbone or the linker, the biologically active agent will be released into the organism over time as the linkage degrades. In this manner, the biologically active agent is delivered to other parts of the organism for treatment of disease or other medical conditions. The released biologically active agent may be in native form, or attached to a linker or the linker and a fragment of the polymer backbone, depending on the placement of the degradable linkage. By tethering or anchoring the biologically active agent to bone, the residence time of the biologically active agent can be increased, which can lead to increased treatment efficacy.

The "therapeutically effective amount" will depend upon a number of factors, including the nature and severity of the condition or disease being treated, the type of biologically active agent being used, the size, age and general health of the subject, and other factors.

The polymeric structure may be administered by various routes, including oral, pulmonary, intravenous, subcutaneous, intramuscular, buccal, nasal, ocular, and rectal. The polymeric structure may also be administered with one or more pharmaceutically acceptable carriers, excipients or diluents.

The hydroxyapatite-targeting polymers of the invention can also be used to bind to other calcium phosphate surfaces or coatings, including hydroxyapatite-coated prosthetic devices and calcium phosphate particles. For example, the hydroxyapatite-targeting polymers of the invention can be used to prevent protein and cell adsorption into prosthetic devices or as part of a synthetically produced delivery device for biologically active agents.

The invention also includes methods of preparing the hydroxyapatite-targeting polymers, and biologically active conjugates thereof, described above. In a preferred embodiment, the activated polymers are prepared by providing a polymeric structure comprising a linear or branched water-soluble and non-peptidic polymer backbone having at least two termini, a first terminus covalently bonded to a first protected chemically reactive group and a second terminus covalently bonded to a second chemically reactive group selected from the group consisting of active carbonates and active esters. Examples of suitable active carbonates and active esters include N-hydroxysuccinimidyl esters, 1-benzotriazolyl esters, N-hydroxysuccinimidyl carbonates and 1-benzotriazolyl carbonates. The second chemically reactive group is reacted with a hydroxyapatite-targeting moiety to form a hydroxyapatite-targeting polymeric structure. The first protected chemically reactive group is preferably selected from the group consisting of protected hydroxyl, protected amine, protected carboxylic acid, protected hydrazide, and protected thiol. In this manner, at least one terminus of the polymer is protected such that the hydroxyapatite-targeting moiety does not attach thereto. This ensures that at least one terminus will be available for subsequent reaction with a biologically active agent. In one embodiment, the following polymer structure is used to react with the hydroxyapatite-targeting moiety:

X—O—CH$_2$CH$_2$O—(CH$_2$CH$_2$O)$_n$—CH$_2$CH$_2$—CO$_2$Y' wherein X is an active carbonate or an active ester, Y' is benzyl, and n is about 3 to about 2000. The method may further include deprotecting the first protected chemically reactive group so that the chemically reactive group is available for reaction, for example with a biologically active agent.

The method of producing a hydroxyapatite-targeting, biologically active polymer preferably includes providing a polymeric structure comprising a linear or branched water-soluble and non-peptidic polymer backbone having at least two termini, a first terminus being covalently bonded to a hydroxyapatite-targeting moiety and a second terminus covalently bonded to a chemically reactive group. The chemically reactive group is reacted with a biologically active agent such that the biologically active agent is attached to the second terminus of the polymeric structure to form a hydroxyapatite-targeting, biologically active polymeric structure. As would be understood by one of ordinary skill, the choice of chemically reactive group will depend on the available functional groups on the biologically active agent. For example, if the biologically active agent contains amine, hydroxyl, or thiol functional groups, an active carbonate or active ester may be used as the chemically reactive group. Particularly preferred chemically reactive groups useful for reacting with biologically active moieties include hydroxyl, amine, carboxylic acid, maleimide, active carbonates and active esters. The biologically active agent preferably comprises peptides, proteins, enzymes, small molecule drugs, dyes, nucleosides, oligonucleotides, lipids, phospholipids, cells, viruses, liposomes, microparticles or micelles. In one embodiment, the biologically active agent has at least one hydroxy group, such as quinidine, camptothecan; and paclitaxel.

The following examples are given to illustrate the invention, but should not be considered in limitation of the invention.

EXAMPLE 1

PEG(2,000)-α-N-CBZ-amine-ω-propionic Acid

To a solution of PEG(2,000)-α-amine-ω-propionic acid (5.0 g, 0.0025 moles) (Shearwater Polymers) in anhydrous methylene chloride (50 ml) N-(benzyloxycarbonyloxy) succinimide (0.80 g 0.0032 moles) and triethylamine (1.0 ml) were added and the reaction mixture was stirred overnight at room temperature under argon atmosphere. Next the reaction mixture was washed with 20 ml phosphate buffer (4%, pH=3), dried with anhydrous magnesium sulfate and added to 400 ml cold diethyl ether. The precipitated product was filtered off and dried under reduced pressure. Yield 4.3 g. NMR ($d_6$-DMSO): 2.44 ppm (t, —$CH_2$—OOC—), 3.14 ppm (q, —$CH_2$NH—(C=O)—O—), 3.51 ppm (s, PEG backbone), 5.01 ppm (s, —$CH_2$—(benzyl)), 7.26 ppm (t, —NH—(C=O)), 7.33 ppm (m, —$C_6H_5$ (benzyl)).

EXAMPLE 2

PEG(2.000)-α-N-CBZ-amine-ω-propionic Acid, N-hydroxysuccinimide Ester

To a solution of PEG(2,000)-α-N-CBZ-amine-ω-propionic acid (4.30 g, 0.00183 moles) in anhydrous methylene chloride (50 ml), N-hydroxysuccinimide (0.22 g, 0.00192 moles) was added following by 1,3-dicyclohexylcarbodiimide (1.0 M solution in methylene chloride, 1.92 ml, 0.00192 moles). The reaction mixture was stirred overnight at room temperature under argon atmosphere. Next the mixture was filtered and solvent was evaporated to dryness. The crude product was dissolved in methylene chloride and precipitated with isopropyl alcohol. The wet product was dried under reduced pressure.

Yield 3.5 g. NMR ($d_6$-DMSO): 2.81 ppm (s, —$CH_2$—$CH_2$-(succinate)), 2.92 ppm (t, —$CH_2$—COO—), 3.14 ppm (q, —$CH_2$NH—(C=O)—O—), 3.51 ppm (s, PEG backbone), 5.01 ppm (s, —$CH_2$-(benzyl)), 7.26 ppm (t, —NH—(C=O)), 7.33 ppm (m, —$C_6H_5$ (benzyl)).

EXAMPLE 3

PEG(2,000)-α-amine-ω-AHPDP

To a solution of PEG(2,000)-α-N-CBZ-amine-ω-propionic acid, N-hydroxysuccinimide ester (3.0 g, 0.00046 moles) in acetonitrile (20 ml), AHPDP-2$Bu_4$ N (0.93 g) and triethylamine (0.25 ml) were added and the reaction mixture was stirred overnight at room temperature under argon atmosphere. Next solvent was evaporated to dryness. The crude product was dissolved in DI water (50 ml) and filtered through Amberlite IR 120 (plus) column (50 ml). The pH of the solution was adjusted to 6.5 with 0.5 M sodium hydroxide and palladium on active carbon (10%) (0.6 g) was added. The mixture was hydrogenated overnight at room temperature under 40 psi of hydrogen. Next the mixture was filtered and water was distilled off under reduced pressure. The wet product was dissolved in methylene chloride (50 ml) then the solvent was distilled off. Finally the product was dried under reduced pressure. Yield 2.3 g.

NMR ($d_6$-DMSO): 1.98 ppm (m, —$CH_2$-(AHPDP)), 2.29 ppm (t, —$CH_2$—CO—), 2.94 ppm (m, —$CH_2$-amine), 3.51 ppm (s, PEG backbone), 7.88 ppm (t, —(C=O)—NH—).

EXAMPLE 4

PEG(2,000)-α-N-Maleimido-ω-AHPDP

To a solution of PEG(2,000)-α-amine-ω-AHPDP (2.0 g, 0.00046 moles) in acetonitrile (20 ml), β-maleimidopropionic acid N-hydroxysuccinimide ester (0.93 g) and triethylamine (0.25 ml) were added and the reaction mixture was stirred overnight at room temperature under argon atmosphere. Next solvent was evaporated to dryness. The crude product was dissolved in methylene chloride and precipitated with isopropyl alcohol. The wet product was dried under reduced pressure. Yield 1.8 g.

NMR ($d_6$-DMSO): 1.98 ppm (m, —$CH_2$-(AHPDP)), 2.29 ppm (t, —$CH_2$—CO—), 3.51 ppm (s, PEG backbone), 7.01 ppm (s, —CH2=CH2-, maleimide), 7.88 ppm (t, —(C=O)—NH-AHPDP), 8.01 ppm (t, —(C=O)—NH-PEG).

EXAMPLE 5

PEG(2,000)-α-hydroxy-ω-propionic Acid, Benzyl Ester

To a solution of PEG(2,000)-α-hydroxy-ω-propionic acid (10 g, 0.0050 moles) (Shearwater Polymers) in anhydrous methylene chloride (100 ml) 1-hydroxybenzotriazole (0.30 g), 4-(dimethylamino)pyridine (1.0 g), benzyl alcohol (10.8 g, 0.100 moles) and 1,3-dicyclohexylcarbodiimide (1.0 M solution in methylene chloride, 7.5 ml, 0.0075 moles) were added. The reaction mixture was stirred overnight at room temperature under argon atmosphere. Next the mixture was concentrated to about 50 ml, filtered and added to 800 ml cold diethyl ether. The precipitated product was filtered off and dried under reduced pressure. Yield 8.2 g.

NMR ($d_6$-DMSO): 2.60 ppm (t, —$CH_2$—COO—), 3.51 ppm (s, PEG backbone), 4.57 ppm (t, —OH—), 5.11 ppm (s, —$CH_2$-(benzyl)), 7.36 ppm (m, —$C_6H_5$ (benzyl)).

EXAMPLE 6

PEG(2,000)-α-benzotriazole Carbonate-ω-propionic Acid, Benzyl Ester

To a solution of PEG(2,000)-α-hydroxy-ω-propionic acid, benzyl ester (8.2 g, 0.0025 moles) in acetonitrile (82 ml), pyridine (0.98 ml) and di(1-benzotriazolyl)carbonate (1.48 g) were added and the reaction mixture was stirred overnight at room temperature under argon atmosphere. Next the mixture was filtered and solvent was evaporated to dryness. The crude product was dissolved in methylene chloride and precipitated with isopropyl alcohol. The wet product was dried under reduced pressure. Yield 6.8 g.

NMR ($d_6$-DMSO): 2.60 ppm (t, —$CH_2$—COO—), 3.51 ppm (s, PEG backbone), 4.62 ppm (m, —$CH_2$—O(C=O)—), 5.11 ppm (s, —$CH_2$-(benzyl)), 7.36 ppm (m, —$C_6H_5$ (benzyl)), 7.60-8.50 ppm (4 m, aromatic protons of benzotriazole).

EXAMPLE 7

PEG(2,000)-α-AHPDP-ω-propionic Acid

To a solution of PEG(2,000)-α-benzotriazole carbonate-ω-propionic acid, benzyl ester (5.7 g, 0.0025 moles) in acetonitrile (40 ml), 3-amino-1-hydroxypropane-1,1-diphosphonic acid, ditetrabutylammonium salt (AHPDP-$2Bu_4N$) (1.92 g) and triethylamine (0.60 ml) were added and the reaction mixture was stirred overnight at room temperature under argon atmosphere. Next, solvent was evaporated to dryness. The crude product was dissolved in DI water (100 ml) and filtered through Amberlite IR 120 (plus) column (50 ml). The pH of the solution was adjusted to 7.2 with 0.5 M sodium hydroxide and palladium on active carbon (10%) (0.6 g) was added. The mixture was hydrogenated overnight at room temperature under 45 psi of hydrogen. Next the mixture was filtered and water was distilled off under reduced pressure. The wet product was dissolved in methylene chloride (150 ml) then the solvent was distilled off. Finally the product was dried under reduced pressure. Yield 4.7 g.

NMR ($d_6$-DMSO): 2.02 ppm (m, —$CH_2$-(AHPDP)), 2.44 ppm (t, —$CH_2$—COO—), 3.51 ppm (s, PEG backbone), 4.03 ppm (m, —$CH_2$—O(C=O)—), 7.11 ppm (t, —(C=O)—NH—).

EXAMPLE 8

PEG(2,000)-α-AHPDP-ω-propionic Acid, N-hydroxysuccinimide Ester

To a solution of PEG(2,000)-α-AHPDP-ω-propionic acid (4.7 g, 0.0020 equivalents) in anhydrous methylene chloride (100 ml), N-hydroxysuccinimide (0.70 g, 0.0024 moles) was added following by 1,3-dicyclohexylcarbodiimide (1.0 M solution in methylene chloride, 2.4 ml, 0.0024 moles). The reaction mixture was stirred overnight at room temperature under argon atmosphere. Next the mixture was filtered and solvent was evaporated to dryness. The crude product was dissolved in methylene chloride and precipitated with isopropyl alcohol. Finally the product was dried under reduced pressure.

Yield 3.6 g. NMR ($d_6$-DMSO): 2.02 ppm (m, —$CH_2$-(AHPDP)), 2.81 ppm (s, —$CH_2$—$CH_2$-(succinate)), 2.92 ppm (t, —$CH_2$—COO—), 3.51 ppm (s, PEG backbone), 4.03 ppm (m, —$CH_2$—O(C=O)—), 7.11 ppm (t, —(C=O)—NH—).

EXAMPLE 9

Coupling of PEG(2,000)-α-AHPDP-ω-propionic Acid, N-hydroxysuccinimide Ester to Proteins Lysozyme was used as a model protein, but any protein can be substituted in its place. Lysozyme (chicken egg white, MW=14,300 Da, 4 mg, 2.8E-7 moles) was dissolved in 2 ml of 50 mM sodium phosphate buffer, pH 7.2. For low degree of PEGylation, approximately 1.1 mg (5.6E-7 moles) of PEG(2,000)-α-AHPDP-ω-propionic acid, N-hydroxysuccinimide ester was added to the lysozyme solution and mixed at room temperature for 5 hours. For high degree of PEGylation, approximately 5.6 mg (2.8E-6 moles) of PEG(2,000)-α-AHPDP-ω-propionic acid, N-hydroxysuccinimide ester was added to the lysozyme solution and mixed at room temperature for 5 hours.

Each PEG-lysozyme multimer (1-PEGmer, 2-PEGmer, 3-PEGmer) was separated on a Superdex 75 size exclusion column (Amersham Pharmacia Biotech) with 5 mM sodium phosphate buffer, pH 7.2 as the elution buffer. Analysis of the purity of the multimers was determined by gel and capillary electrophoresis. Each purified multimer was used to determine the efficiency of conjugate binding to hydroxyapatite.

EXAMPLE 10

Binding of PEG(2,000)-α-AHPDP-ω-protein to Hydroxyapatite In Vitro

Hydroxyapatite (Fast Flow, Fluka, 120 mg) was equilibrated in 1 ml of 5 mM sodium phosphate buffer, pH 7.2 for 24 hours at 37° C. Native lysozyme or the PEG-lysozyme conjugate was mixed with the hydroxyapatite suspension in a 1:1 volume ratio and stirred at 37° C. Samples were taken from the mixture at various time points and analyzed for the percentage of unbound protein or PEG-protein conjugate by gel permeation chromatography. Native lysozyme did not adsorb to hydroxyapatite while 100% of the 3-PEGmer and 2-PEGmer adsorbed by $1^{1/2}$ hour incubation. The 1-PEGmer conjugate had limited adsorption after $1^{1/2}$ hour incubation. All samples had similar protein concentrations.

EXAMPLE 11

PEG(2,000)-α-methoxy-ω-$_L$-tyrosine

To a solution of PEG(2,000)-α-methoxy-ω-amine (2.0 g, 0.0010 moles) (Shearwater Polymers) in anhydrous acetonitrile (30 ml) N-CBZ-$_L$-tyrosine p-nitrophenyl ester (0.42 g 0.0010 moles) and triethylamine (0.3 ml) were added and the reaction mixture was stirred overnight at room temperature under argon atmosphere. Next the solvent was distilled off under reduced pressure. The residue was dissolved in 200 ml DI water and the resulting solution was filtered through anion exchange resin (to remove p-nitrophenol) and palladium on active carbon (10%) (0.3 g) was added. The mixture was hydrogenated overnight at room temperature under 40 psi of hydrogen. Next the mixture was filtered and the product was extracted with methylene chloride. The extract was dried with anhydrous magnesium sulfate and solvent was distilled off under reduced pressure. The wet product was dried under reduced pressure. Yield 1.25 g.

NMR ($d_6$-DMSO): 2.62 ppm and 2.82 ppm (m, —$CH_2$-(tyrosine)), 3.23 ppm (s, —$OCH_3$), 3.51 ppm (s, PEG backbone), 4.12 ppm (m, CH-(tyrosine)), 6.64 ppm and 6.97 ppm (2 m, aromatic protons of tyrosine), 7.86 ppm (t, —(C=O)—NH-PEG).

EXAMPLE 12

PEG(2,000)-α-N-CBZ-$_L$-tyrosine-ω-propionic Acid

To a solution of PEG(2,000)-α-amino-ω-propionic acid (2.50 g, 0.0012 moles) (Shearwater Polymers) in anhydrous acetonitrile (30 ml) N-CBZ-$_L$-tyrosine p-nitrophenyl ester (0.54 g 0.0012 moles) and triethylamine (0.5 ml) were added and the reaction mixture was stirred overnight at room temperature under argon atmosphere. Next the solvent was distilled off under reduced pressure. The residue was dissolved in 220 ml DI water and the resulting solution was filtered through anion exchange resin to remove p-nitrophenol. NaCl (20 g) was added and the pH of the solution was adjusted to 3.0 with 5% phosphoric acid. The product was extracted with methylene chloride. The extract was dried with anhydrous magnesium sulfate and solvent was distilled off under reduced pressure. The wet product was dried under reduced pressure. Yield 1.75 g.

NMR (d$_6$-DMSO): 2.44 ppm (t, —CH$_2$—COO—), 2.62 ppm and 2.82 ppm (m, —CH$_2$-(tyrosine)), 3.51 ppm (s, PEG backbone), 4.12 ppm (m, CH-(tyrosine)), 4.94 ppm (m, —CH$_2$-(benzyl)), 6.64 ppm and 7.04 ppm (2 m, aromatic protons of tyrosine), 7.25 ppm (d, —(C=O)—NH-tyrosine), 7.32 ppm (m, —C$_6$H$_5$ (benzyl)), 8.01 ppm (t, —(C=O)—NH-PEG).

EXAMPLE 13

PEG(2,000)-α-N-CBZ-$_L$-tyrosine-ω-propionic Acid, N-hydroxysuccinimide Ester

To a solution of PEG(2,000)-α-N-CBZ-$_L$-tyrosine-ω-propionic acid (1.66 g, 0.00070 moles) in anhydrous methylene chloride (20 ml), N-hydroxysuccinimide (0.089 g, 0.00077 moles) was added following by 1,3-dicyclohexylcarbodiimide (1.0 M solution in methylene chloride, 0.77 ml, 0.00077 moles). The reaction mixture was stirred overnight at room temperature under argon atmosphere. Next the mixture was filtered and solvent was evaporated to dryness. The crude product was dissolved in methylene chloride and precipitated with isopropyl alcohol. The wet product was dried under reduced pressure. Yield 1.26 g.

NMR (d$_6$-DMSO): 2.62 ppm and 2.82 ppm (m, —CH$_2$-(tyrosine)), 2.81 ppm (s, —CH$_2$—CH$_2$-(succinate)), 2.92 ppm (t, —CH$_2$—COO—), 3.51 ppm (s, PEG backbone), 4.12 ppm (m, CH-(tyrosine)), 4.94 ppm (m, —CH$_2$-(benzyl)), 6.64 ppm and 7.04 ppm (2 m, aromatic protons of tyrosine), 7.25 ppm (d, —(C=O)—NH-tyrosine), 7.32 ppm (m, —C$_6$H$_5$(benzyl)), 8.01 ppm (t, —(C=O)NH-PEG).

EXAMPLE 14

PEG(2,000)-α-tyrosine-ω-AHPDP

To a solution of PEG(2,000)-α-N-CBZ-$_L$-tyrosine-ω-propionic acid, N-hydroxysuccinimide ester (1.15 g, 0.00046 moles) in acetonitrile (15 ml), AHPDP-2Bu$_4$ N (0.36 g) and triethylamine (0.10 ml) were added and the reaction mixture was stirred overnight at room temperature under argon atmosphere. Next solvent was evaporated to dryness. The crude product was dissolved in DI water (50 ml) and filtered through Amberlite IR 120 (plus) column (20 ml). The pH of the solution was adjusted to 6.5 with 0.5 M sodium hydroxide and palladium on active carbon (10%) (0.3 g) was added. The mixture was hydrogenated overnight at room temperature under 40 psi of hydrogen. Next the mixture was filtered and water was distilled off under reduced pressure. The wet product was dissolved in methylene chloride (50 ml) then the solvent was distilled off. Finally the product was dried under reduced pressure. Yield 0.65 g.

NMR (d$_6$-DMSO): 2.02 ppm (m, —CH$_2$-(AHPDP)), 2.29 ppm (t, —CH$_2$—CO—), 3.51 ppm (s, PEG backbone), 4.13 ppm (m, —CH-(tyrosine)), 6.70 ppm and 7.01 ppm (2 m, aromatic protons of tyrosine), 7.94 ppm (d, —(C=O)—NH-AHPDP), 8.01 ppm (t, —(C=O)—NH-PEG).

EXAMPLE 15

Binding of PEG(2,000)-α-$_L$-tyrosine-ω-AHPDP and Other PEG-AHPDP Derivatives to Hydroxyapatite In Vitro Hydroxyapatite (Fast Flow, Fluka, 12 mg) was equilibrated in 1 ml of 5 mM sodium phosphate buffer, pH 7.2 for 24 hours at 37° C. AHPDP, PEG(2,000)-α-methoxy-ω-hydroxy, PEG (2,000)-α-methoxy-ω-$_L$-tyrosine, PEG(5,000)-α-amine-ω-AHPDP, and PEG(2,000)-α-$_L$-tyrosine-ω-AHPDP derivatives at concentrations ranging from 0.1 mg/ml to 1.0 mg/ml in 5 mM sodium phosphate buffer, pH 7.2 were individually mixed with the hydroxyapatite suspension in a 1:1 volume ratio and stirred at 37° C. Samples were taken from each mixture at various time points and analyzed for the percentage of unbound PEG or PEG-AHPDP derivative by gel permeation chromatography. PEG(2,000)-α-methoxy-ω-hydroxy and PEG(2,000)-α-methoxy-ω-$_L$-tyrosine did not show any adsorption to hydroxyapatite while the PEG-AHPDP derivatives showed 100% adsorption by 8 hours of incubation. AHPDP had an adsorption half-life of around 1 min while the PEG(5,000)-α-amine-ω-AHPDP and PEG(2,000)-α-$_L$-tyrosine-ω-AHPDP derivatives had a 45 minute and 19 minute adsorption half-life, respectively.

EXAMPLE 16

Excretion Study of PEG(2,000)-α-$_L$-tyrosine$^{/125}$-ω-AHPDP in Mice

PEG(2,000)-α-$_L$-tyrosine-ω-AHPDP and mPEG(2,000)-α-$_L$-tyrosine were iodinated using a standard chloramine-T procedure (Bolton, *Methods Enzymol*. 124: 18-29, 1986). In brief, a 15 μL aliquot of PEG(2,000)-α-$_L$-tyrosine-ω-AHPDP or mPEG(2,000)-α-$_L$-tyrosine (2 μg/μl it total weight) was mixed with 50 μL of 5 μmM phosphate buffer. To this was added 1 mCi of NaI$^{125}$ and 10 μL of Chloramine-T (1 μg/μL). The mixture was finger vortexed for 30 s followed by addition of 100 μL of L-Cys (2 .mu.g/.mu.L), followed by another 30 s of finger vortexing. The purification was carried out by reverse-phase chromatography. The samples were eluted at 37° C. using a curvilinear gradient of 0.1% trifluoroacetic acid (TFA) in acetonitrile (19-63%) versus 0.1% aqueous TFA over 30 min at 1.5 ml.min$^{-1}$.

Male ICR mice (20-25 g) were administered either 2 μCi of PEG(2,000)-α-$_L$-tyrosine-ω-AHPDP or mPEG(2,000)-α-$_L$-tyrosine via tail vein injection (100 μL; i.v.). The mice were placed into metabolism cages and urine and feces were collected at the following time points (1, 2, 3, 4, 6, & 8 hr post-injection) (n=6). The samples were counted on a gamma counter and the counts were converted to a percentage of total counts injected. mPEG(2,000)-α-$_L$-tyrosine had an average % [$^{125}$I] captured of 47.5 with greater than 95% of radiolabeled compound being excreted in the urine. PEG(2,000)-α-$_L$-tyrosine-ω-AHPDP had a significantly lower percentage (5-fold) of [$^{125}$I] captured (7.7%) during the 8 hour time course than the mPEG(2,000)-α-$_L$-tyrosine and again ~95% of the radiolabeled compound was excreted in the urine. The two compounds produced similar excretion profiles over the 8-hour period with the exception that PEG(2,000)-α-$_L$-tyrosine-ω-AHPDP produced a significantly greater percentage of [$^{125}$I] retained in the body.

EXAMPLE 17

PEG(10,000)-(α-AHPDP)$_4$

To a solution of PEG(10,000)-(α-benzotriazole carbonate)$_4$ (Shearwater Polymers) (4.2 g, 0.00042 moles) in acetonitrile (40 ml), 3-amino-1-hydroxypropane-1,1-diphosphonic acid, ditetrabutylammonium salt (AHPDP-2Bu$_4$N) (1.32 g) and triethylamine (0.4 ml) were added and the reaction mixture was stirred overnight at room temperature under argon atmosphere. Next, solvent was evaporated to dryness. The crude product was dissolved in DI water (100 ml) and filtered through Amberlite IR 120 (plus) column (50 ml). Next the water was distilled off under reduced pressure. The wet product was dissolved in methylene chloride (150 ml) then the solvent was distilled off. Finally the product was dried under reduced pressure. Yield 3.1 g.

NMR (d$_6$-DMSO): 2.02 ppm (m, —CH$_2$-(AHPDP)), 3.51 ppm (s, PEG backbone), 4.03 ppm (m, —CH$_2$—O (C=O)—), 7.11 ppm (t, —(C=O)—NH—).

EXAMPLE 18

PEG(3,400)-α-CBZ-amine-ω-propionic Acid, Quinidine Ester

Reaction Scheme:

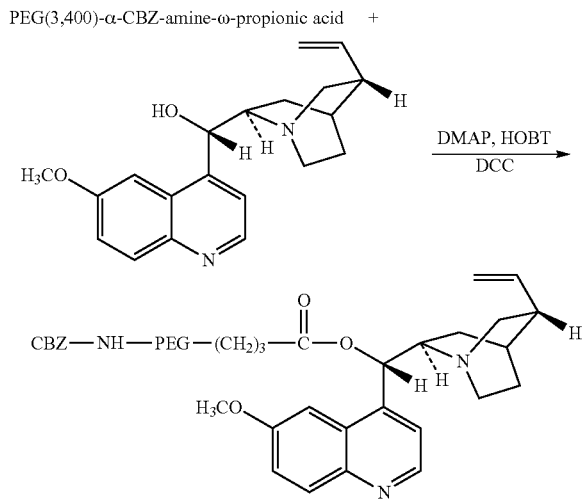

PEG(3,400)-α-CBZ-amine-ω-propionic acid (Shearwater Corporation) (3.40 g, ~1.00 mmol), quinidine (0.49 g, ~1.50 mmol), HOBT (catalytic amount), and DMAP (0.15 g, ~1.23 mmol) were dissolved in CH$_2$Cl$_2$ (100 ml). The solution was treated with DCC (0.31 g, ~1.50 mmol) that was dissolved in CH$_2$Cl$_2$ (3 ml) and was allowed to stir at room temperature under argon overnight (~8 h). The solvent was removed in vacuo and the residual syrup was dissolved in toluene (25 ml) and filtered through a plug of celite. The toluene was removed in vacuo and the syrup was dissolved in CH$_2$Cl$_2$ (5 ml). Addition to diethyl ether yielded the product as a white precipitate, which was collected by filtration and dried under vacuum (Yield 2.77 g, ~81%).

EXAMPLE 19

PEG(3,400)-α-amine-ω-propionic Acid, Quinidine Ester

PEG(3,400)-α-CBZ-amine-ω-propionic acid, quinidine ester (2.50 g) was dissolved in ethyl alcohol and palladium on active carbon (10%) (0.5 g) was added. The mixture was hydrogenated overnight at room temperature under 40 psi of hydrogen. Next the mixture was filtered and ethanol was distilled off under reduced pressure. Yield 2.1 g. NMR spectrum of the product showed that the amine group connected to PEG backbone was completely deprotected.

EXAMPLE 20

PEG(5,400)-α-AHPDP-ω-propionic Acid, Quinidine Ester

To a solution of PEG(2,000)-α-AHPDP-ω-propionic acid, NHS ester (1.22 g, 0.00050 moles) in anhydrous methylene chloride (100 ml), PEG(3,400)-amine-ω-propionic acid, quinidine ester (1.89 g, 0.00050 moles) was added followed by triethylamine (0.10 ml). The mixture was stirred overnight under argon atmosphere. Next the reaction product was precipitated with ethyl ether and dried under reduced pressure. Yield 3.01 g Gel permeation chromatography showed that product with molecular weight 5,700 Da was formed (98%). Hydrolysis half-life of the ester in PEG(5,400)-α-AHPDP-ω-propionic acid, quinidine ester in buffer at pH 7.3 is 239 h (@22° C.) and 46 h (@37° C.) leading to the release of quinidine.

What is claimed is:
1. A method for attaching a hydroxyapatite-targeting water-soluble polymer to a surface or device, said method comprising the steps of:
  a) providing a water-soluble polymer comprising at one terminus, a hydroxyapatite-targeting moiety, and
  b) binding the water-soluble polymer from step (a) with a hydroxyapatite- or calcium phosphate-coated prosthetic or drug delivery device or surface under conditions effective to promote said binding.
2. The method of claim 1, wherein the water-soluble polymer is selected from the group consisting of poly(alkylene glycol), poly(oxyethylated polyol), poly(olefinic alcohol), poly(vinylpyrolidone), poly(hydroxypropylmethacrylamide), poly(α-hydroxy acid), poly(vinyl alcohol), polyphosphazene, polyoxazoline, and copolymers and terpolymers thereof.
3. The method of claim 2, wherein the water-soluble polymer is a poly(alkylene glycol).
4. The method of claim 3, wherein the water-soluble polymer is a poly(ethylene glycol).
5. The method of claim 4, wherein the poly(ethylene glycol) is linear.
6. The method of claim 4, wherein the poly(ethylene glycol) is branched.

7. The method of claim 4, wherein the water-soluble polymer has a molecular weight ranging from about 100 daltons to about 100,000 daltons.

8. The method of claim 7, wherein the water-soluble polymer has a molecular weight ranging from about 6,000 daltons to about 80,000 daltons.

9. The method of claim 1, wherein the hydroxyapatite-targeting moiety is selected from the group consisting of tetracycline, calcein, bisphosphonates, polyaspartic acid, polyglutamic acid, and aminophosphosugars.

10. The method of claim 1, wherein the hydroxyapatite-targeting moiety is a bisphosphonate.

11. The method of claim 10, wherein the bisphosphonate is selected from the group consisting of etidronate, alendronate, and 3-amino-1-hydroxypropane-1-1-diphosphonic acid (AHPDP).

12. The method of claim 10, wherein the water-soluble polymer is a poly(ethylene glycol).

13. The method of claim 1, wherein the water-soluble polymer comprises at a second terminus, a biologically active agent.

14. The method of claim 1, wherein the water-soluble polymer comprises at a second terminus, a protecting group.

15. The method of claim 14, wherein the protecting group is protected hydroxyl.

16. The method of claim 1, wherein said binding comprises incubating the hydroxyapatite or calcium phosphate coated prosthetic or drug delivery device or surface with a solution comprising the hydroxyapatite-targeting water-soluble polymer under conditions effective to promote binding thereto.

17. A hydroxyapatite- or calcium phosphate-coated prosthetic or drug delivery device or surface comprising a water-soluble polymer having at one terminus, a hydroxyapatite-targeting moiety, bound thereto.

* * * * *